United States Patent
Fine et al.

(10) Patent No.: US 11,243,197 B1
(45) Date of Patent: Feb. 8, 2022

(54) METHOD AND APPARATUS FOR CALIBRATION OF GAS AND LIQUID CONCENTRATION SENSORS WITHOUT THE NEED FOR KNOWN CALIBRATION STANDARDS

(71) Applicant: VERO Biotech LLC, Atlanta, GA (US)

(72) Inventors: David H. Fine, Cocoa Beach, FL (US);
Edward Bromberg, Orlando, FL (US);
Thorsten Schmidt, Cocoa, FL (US);
Ryan Denton, Titusville, FL (US)

(73) Assignee: VERO Biotech LLC, Atlanta, GA (US)

( * ) Notice: Subject to any disclaimer, the term of this patent is extended or adjusted under 35 U.S.C. 154(b) by 230 days.

(21) Appl. No.: 16/513,274

(22) Filed: Jul. 16, 2019

Related U.S. Application Data

(60) Provisional application No. 62/699,774, filed on Jul. 18, 2018.

(51) Int. Cl.
*G01N 33/00* (2006.01)
*G01N 27/416* (2006.01)

(52) U.S. Cl.
CPC ..... *G01N 33/0006* (2013.01); *G01N 27/4163* (2013.01); *G01N 33/0037* (2013.01)

(58) Field of Classification Search
CPC .......... G01N 33/0006; G01N 27/4163; G01N 33/0037
See application file for complete search history.

(56) References Cited

U.S. PATENT DOCUMENTS

| | | | | |
|---|---|---|---|---|
| 9,279,794 B2 * | 3/2016 | Tolmie | ............... | G01N 33/0037 |
| 2008/0296174 A1 * | 12/2008 | Ding | ................. | G01N 27/4175 205/781 |
| 2017/0095634 A1 * | 4/2017 | Miller | .................. | A61M 16/12 |

* cited by examiner

*Primary Examiner* — David Z Huang (57) ABSTRACT

A device and method for calibrating a NO delivery device using NO and $NO_2$ measurements, without using a known standard.

19 Claims, 5 Drawing Sheets

METHOD AND APPARATUS FOR CALIBRATION OF GAS AND LIQUID CONCENTRATION SENSORS WITHOUT THE NEED FOR KNOWN CALIBRATION STANDARDS

CROSS REFERENCE TO RELATED APPLICATIONS

The present application claims priority to U.S. Provisional Pat. App. Ser. No. 62/699,774, entitled "Methods and Apparatus for Calibration of Gas and Liquid Concentration Sensors without the Need for Known Calibration Standards," filed Jul. 18, 2018, the entire disclosure of which hereby incorporated by reference.

TECHNICAL FIELD

The invention relates primarily to the calibration of gas sensors, but the invention applies equally to sensors that measure analytes in solutions.

BACKGROUND

Nitric Oxide (NO) also known as the nitrosyl radical, is a free radical that is an important signaling molecule. For example, NO can cause smooth muscles in blood vessels to relax, thereby resulting in vasodilation and increased blood flow through the blood vessel. These effects can be limited to small biological regions since NO can be highly reactive with a lifetime of a few seconds and can be quickly metabolized in the body.

Some disorders or physiological conditions can be mediated by inhalation of NO. The use of low concentrations of inhaled NO can prevent, reverse, and/or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, haline membrane disease, acute pulmonary thromboembolism, heparin-protamine reactions, sepsis, asthma and status asthmaticus or hypoxia. NO can also be used to treat chronic pulmonary hypertension, bronchopulmonary dysplasia, chronic pulmonary thromboembolism and/or idiopathic and/or primary pulmonary hypertension or chronic hypoxia.

Generally, NO can be inhaled or otherwise delivered to the individual's lungs. Providing a therapeutic dose of NO can treat a patient suffering from a disorder or physiological condition that can be mediated by inhalation of NO or supplement or minimize the need for traditional treatments in such disorders or physiological conditions. Typically, the NO gas can be supplied in a bottled gaseous form diluted in nitrogen gas ($N_2$). Great care should be taken to prevent the presence of even trace amounts of oxygen ($O_2$) in the tank of NO gas because the NO, in the presence of $O_2$, can be oxidized to nitrogen dioxide ($NO_2$). Unlike NO, $NO_2$ can be highly toxic at the part per million level if inhaled, and can form nitric and nitrous acid in the lungs.

FDA approved devices for delivering inhaled NO are typically calibrated before being used on a patient, and then at regular intervals, which could be once a day, or less frequently up to once a month or more, depending upon the circumstances. Sometimes more frequent calibration is needed. The calibration consists of checking the detector, also called a sensor, that senses and reports the concentration of the drug, NO, that is being delivered to the patient. The calibration also consists of checking the detector that senses and reports on $NO_2$ impurity in the gas being delivered to the patient. Monitoring the $O_2$ concentration may also be desirable, particularly for systems that use NO diluted in $N_2$. For NO and $NO_2$ sensors, it is typically desirable to determine both the zero drift and the response to a test gas\. For $O_2$ sensors, typically an air control is sufficient.

According to known methods, NO and $NO_2$ sensors are calibrated directly with accurately known gas standards that are stored in gas tanks, also called gas cylinders, that are under pressure of from approximately 200 psig up to 2,400 psig. Since the measurement range for NO is typically in the 1 to 160 parts per million (ppm) range and for $NO_2$ is in the 0.1 to 5 ppm range, the gas standards are typically in this concentration range. Low ppm gas standards, like all low concentration standards are difficult, if not impossible, to store for long periods of time (months to years), due to sticking of the low concentration analyte molecules on active sites of the container wall. In addition, every time the calibration gas is withdrawn from the calibration cylinder, great care has to be taken to prevent even a very minute amount of air from back-streaming into the cylinder. Every molecule of oxygen that enters the cylinder will react with an NO molecule in the tank and form $NO_2$, and every molecule of water will react with an $NO_2$ molecule to form nitric acid and/or nitrous acid. As a result, even with precautions, the number of times a calibration standard can be withdrawn from the calibration tank without causing significant degradation of the concentration of the standard is limited. While dilution from a higher concentration immediately prior to use can be accomplished in a laboratory, it requires a highly pure dilution gas and accurate mass flow controllers, and is difficult and complex to carry out in the field, such as in a neonatal, pediatric or adult Intensive Care Unit (ICU), with critically ill patients, or at the bedside of a patient in a hospital room. Furthermore, for gas standards, one has to rely on the manufacturer of the gas standard for both the accuracy of the standard, and for how well the tank was prepared, which determines how long the accuracy will be maintained in the gas cylinder. The same is true for storing low concentration standards in solution, and low ppm level standards of analytes in ionic and non-ionic solutions are not available for purchase. Instead, high concentration standards are purchased or made up and stored at much higher concentrations, where the losses to the container walls are not as important, and diluted immediately prior to use. Even in a wet chemistry laboratory, the preparation of ppm concentration level standards can be tedious and time consuming, usually requiring fresh standards to be made up daily or even more frequently.

For patients prescribed inhaled NO in a clinical setting, it would be highly desirable to accurately calibrate devices that deliver NO for inhalation therapy, without the need for special, accurate and certified NO and $NO_2$ calibration gases at low ppm concentrations, and the need to deliver such calibration gases to check and confirm the accuracy of the NO and $NO_2$ gas sensors. Gas calibrators based on permeation tubes, work well in a laboratory setting, but are too complex to be useful in a clinical setting since they require highly precise temperature control, the availability of highly pure dilution gas, measurement of gas flows with mass flow controllers, and precision microgram mass balance. Dynamic gas calibrators that utilize real-time dilution of high concentration standards, require the availability of the purified diluent gas, and the precise mixing with calibrated mass flow controllers. To achieve low ppm levels, a second stage dilution is often necessary.

SUMMARY

Embodiments described herein generally relate to the replacement of test gas standards, which are typically NIST traceable, with an unknown concentration of the analyte of interest and comparing the rate of gain and/or loss of the analyte with the known chemical kinetics, so as to accurately calculate the rate of change and hence determine the concentration of the analyte. Methods described herein not only do not require the need for accurately known and certified standards, but can be more reliable and more accurate than classical methodology using known standards.

In one aspect, a method for tankless calibration of a NO sensor device and/or a $NO_2$ sensor device can include obtaining a gas in a closed volume, the gas including NO (for example, where the concentration of NO is not well known), and $O_2$, wherein the $O_2$ content exceeds the NO concentration, measuring a change in NO signal and/or an increase in the $NO_2$ signal, and then sampling the gas over a time frame, calculating a rate of loss of NO signal and a rate of increase of the $NO_2$ signal, determining whether the sum of the NO signal and the $NO_2$ signal is substantially constant over the time frame; establishing the NO concentration from the rate of loss of NO signal and/or establishing the $NO_2$ concentration from the rate of increase of the $NO_2$ signal, and, optionally, recalibrating the NO and/or the $NO_2$ sensor according to the now accurately established NO and/or $NO_2$ concentrations.

In another aspect, a method for confirming calibration of a NO sensor device can include obtaining a gas in a closed volume, the gas including NO and oxygen, wherein the oxygen content is known, measuring a change in NO concentration and/or $NO_2$ concentration, by sampling the gas at a specific time after obtaining the gas, calculating an original concentration of NO based on the specific time, the known $O_2$ content, and the measured NO concentration and/or the measured $NO_2$ concentration, and determining whether the original concentration is accurate.

In some embodiments, the time frame can be about 15 to 30 seconds to 1 to 4 minutes.

In some embodiments, the closed volume can be between 0.5 and 1 liter of gas.

In some embodiments, obtaining the gas in the closed volume can include filling the closed volume with the gas generated by a gas generation portion of the device.

In some embodiments, the method can include comparing the rate of loss of NO signal and/or the rate of increase of the $NO_2$ signal at two or more different NO starting concentrations, to determine that the rates vary by the square power of the starting NO concentration.

In some embodiments, the NO signal can decrease by the same amount that the $NO_2$ signal increases.

In some embodiments, the $O_2$ content can exceed the NO concentration by at least a factor of 10, 100, 1,000, 10,000, 100,000 and often by a factor of 200,000.

Other features, objects, and advantages will be apparent from the description, drawings, and claims.

DETAILED DESCRIPTION

The administration of NO to patients can be improved by developing simplified methods for more efficiently and accurately calibrating NO delivery systems. Such systems can promote a more pure, controlled and accurate delivery of NO, which achieves enhanced efficiency, safety, and clinical efficacy.

A method of checking on the calibration accuracy of the sensors can be performed monthly. The elapsed time for a calibration check can be about 1 to 2 to 3 to 4 to 5 minutes. The calibration check can be fully automated and can be performed before or during normal operation (with a dual sensor delivery platform such as provided by Vero Biotech), or at any other time.

According to methods described herein, there is no need to have prior knowledge of the precise NO concentration, and special calibration gases are not required. For chemiluminescent gas analyzers which are widely used in air pollution measurements, the NO concentration should be greater than about 10 ppm, so as to give NO and $NO_2$ changes that can be accurately determined by the accuracy of the analyzer. For electrochemical sensors, which are widely used in NO inhalation in a hospital setting, the starting NO concentration should be greater than about 30 to 80 ppm to be in their operating range for times as short as a few minutes. For the $NO_2$ sensor, the $NO_2$ concentration can start at zero, and build up as the NO is oxidized to $NO_2$. For longer reaction times, lower NO concentrations can be used. If more sensitive electrochemical sensors become available, then the starting NO concentration can be reduced accordingly.

Whatever the NO concentration, the $NO_2$ concentration would go up and the NO concentration would go down by the same amount. The NO and $NO_2$ concentration at the starting time, time zero, can then be back-calculated. For example, based on an established look up table, at one minute an $NO_2$ formation of 1.8 ppm in air can only be formed if the NO concentration was 80 ppm. Stated another way, the formation of 1.8 ppm of $NO_2$ in 60 seconds in air can only occur if the NO concentration was 80 ppm. Further computation would show an effective doubling at 2 minutes, since the formation is linear with time over relatively small concentration changes.

Another way of using the equation described below is to measure the decay of the NO signal with time. A NO reading of 78.2 at 1 minute, 76.5 at 2 minutes, 74.9 at 3 minutes, 74.4 at 4 minutes and 71.8 at 5 minutes corresponds to a starting NO concentration of 80 ppm. This example is for a 5 minute time interval. However, continuous data collection would allow the determination to be made within a minute or less, even within 30 seconds or within 10 seconds. In this example, if the data were collected every 0.5 seconds, then over a period of 10 seconds, 30 seconds, 1 minute, or up to about 5 minutes, the slope of the straight line plot of concentration versus time should be linear; if the sensors are working properly then the linear regression R value of the plot should be greater than 0.99. Indeed, an R value of >0.99 becomes a measure of the confidence level of the calibration. An R value of say 0.75 would suggest that the data was too scattered to place a high confidence level in the accuracy of the calibration.

A further check, if required, can be to repeat the calibration at a different NO concentrations. Since the $NO_2$ concentration, and the NO loss, is proportional to the square power of the NO concentration, this too adds a very powerful confirmation to the accuracy of the quantitative calibration.

The formation is also linearly proportional to the oxygen concentration. Varying the $O_2$ concentration can add another dimension to the calibration method.

Thus, four independent quantitative calibration information factors can be derived:
(1) The sum of $NO+NO_2$ remains constant.
(2) The increase in the $NO_2$ concentration can be used to calculate the NO concentration, and back calculated to zero time. This calculation can be repeated at each time point, and should give the same NO value. The reverse is also true, in that knowing the NO concentration can be used to calculate the $NO_2$ concentration.
(3) If the NO concentration is varied, by a factor of 2, for example, then the $NO_2$ concentration would be expected to increase by a factor of 4 (the second power effect). If the starting NO concentration was increased to 160 ppm of NO in air, then at 60 seconds, the NO loss would be 4 times the loss at 80 ppm and the $NO_2$ gain would be 4 times higher.
(4) The $NO_2$ concentration is proportional to the $O_2$ concentration. Doubling the 02 concentration, for example, would double the NO loss and double the NO gain.

This potential quadruple check on the accuracy of the NO and $NO_2$ sensors provides far more confidence, precision and accuracy to the calibration and assures the user that the sensors are operating as specified. This quadruple check cannot be achieved with a single gas calibration standard.

At a fixed $O_2$ concentration such as air, and a set time, like 1 or 2 or 3 or 4 or 5 minutes, there are unique NO and $NO_2$ concentrations which could occur. Measurement of both NO and $NO_2$ within the calculated range, would be confirmation of the calibration. Varying the $O_2$ and or the NO concentration and/or the time, would add to the confidence level and provide additional confirmatory data and increase the confidence in the calibration. The theoretical curves show the loss of NO and the corresponding gain in $NO_2$, from time zero.

Current clinical devices that are available for NO inhalation work, with the NO sensors typically based on electrochemistry. Such devices typically have a linear response, so that if the devices are calibrated at zero concentration and a concentration close to full scale, then the straight line joining the two points is the calibration curve over the complete range. Examples of commercial suppliers of these sensors include Citicells and Alphasense.

Conventional calibration procedures involve the use of specially made and certified calibration gases. One supplier of these calibration gases is Air Liquide, which provides small disposable aluminum cylinders. Known calibration procedures involve taking the calibration gas cylinders, one with NO in nitrogen and the other with $NO_2$ in air, to the NO delivery device and switching the instrument to the calibration mode. A small gas flow from the cylinder is allowed to flow past the sensors and the instrument response is compared with the previous calibration. If any drift has occurred, the calibration settings are reset. Similarly, the zero control is set by sampling ambient air and checking that the zero level has not changed with time. Since treatments with concentrations at 1 ppm or below may sometimes be needed, in order to increase the accuracy of the device under these use conditions, instead of using ambient air to set the zero, the ambient air is first purified by passing it through a scrubber to remove potential NO and $NO_2$ contaminants prior to performing the zero calibration. During calibration with gas standards, the NO delivery devices are typically not sensing the concentration of NO and $NO_2$ gas that is being delivered to the patient, unless they have been equipped with dual NO and/or $NO_2$ sensors. Calibration with gas standards is a tedious and complex process in a clinical setting, and typically has to be carried out for every patient. It requires training and experience with the equipment in order to accomplish the proper procedure. Even then, it is important to recognize that the measured values cannot be assumed to be perfectly accurate due to degradation of the standards with time. For a good calibration standard that is within specification, these errors can be of the order of 5 to 10%.

NO is a selective pulmonary vasodilator that is approved in the US for the treatment of Persistent Pulmonary Hypertension of the Newborn (PPHN). NO is delivered by diluting trace amounts of NO into oxygen enriched gases that are being delivered to a patient by a ventilatory assist device. The NO content of the gas that is being delivered to the patient is monitored continuously. See, Guidance Document for Premarket Notification Submissions for NO Delivery Apparatus, NO Analyzer and Nitrogen Dioxide Analyzer. Food and Drug Administration, Department of Health and Human Services. Jan. 24, 2000, which is incorporated by reference in its entirety. Commercial NO gas delivery systems use electrochemical gas sensors. The accuracy of the NO dose that is delivered to the patient is dependent upon the accuracy and precision of the method that is used to calibrate the NO sensors. As an example, a gas standard that had degraded to half of its certified value would lead to a patient being overdosed by a factor of two.

When NO is diluted into a gas that contains oxygen ($O_2$), the toxic byproduct $NO_2$ is formed. FDA requires that the $NO_2$ content of the gas being delivered to the patient be monitored to ensure that the $NO_2$ concentration remains below acceptable environmental levels, as required by FDA in the Guidance Document referred to above.

In order to deliver the correct NO dose to the patient, it is important, and in many cases essential, that the embedded NO sensor is working and is properly calibrated. The sensor needs to be calibrated, both for drift of the zero and for the full scale measurement. The calibration method that is currently in use for the full scale measurement is based upon the classical analytical laboratory procedure of using accurately known gas standards, supplied from a high pressure metal cylinder.

The manufacture of accurate and stable calibration standards are always difficult at low ppm concentrations, because the compound of interest tends to "stick" to active sites on the interior walls of the containing vessel. For an NO concentration of approximately 45 ppm, the calibration standard is supplied in pure nitrogen, with care being taken to remove all traces of $O_2$, so as to prevent the in situ oxidation of NO to $NO_2$.

$$2\ NO+O_2=2NO_2$$

The $NO_2$ calibration standard is typically supplied in air that is free of moisture, since $H_2O$ reacts with $NO_2$ to form nitric and nitrous acids.

$$2NO_2+H_2O=HNO_2+HNO_3$$

In addition, $NO_2$ is highly polar and tends to be especially "sticky" on the active surface sites leading to the rapid loss of $NO_2$ during storage. The Center for Disease Control (CDC) has reported that a cylinder of $NO_2$ gas in $N_2$ and another in air degraded in one month from 10 ppm to 8.13 ppm and 10 ppm to 6.88 ppm, respectively. See, for example, Chilton, J. E., Timko, R. J., and Chuhta, E. J. U.S. Department of Health and Human Services, Public Health Service, Centers for Disease Control and Prevention, National Institute for Occupational Safety and Health, DHHS (NIOSH) Publication No. 2006-104, Information Circular 9482, 2005 December; p. 1-14, which is incorporated by reference in its entirety. A portable calibration gas cylinder, labeled to contain 2 ppm $NO_2$, was found to contain only 0.9 ppm $NO_2$ a month later.

In the laboratory, calibration gases are typically supplied in aluminum cylinders at pressures of the order of 2,000 psi. In use, these cylinders require a two stage gas regulator, with a shut off valve. In order to prevent back streaming of air into these cylinders, a special vacuum manifold should be used between the cylinder and the regulator, because back streaming of even minute amounts of air will reduce the concentration in the NO cylinder by oxidation of the NO with whatever molecules of oxygen entered the cylinder. See, for example, Sokol, G. M., Van Meurs, K. P., Wright, L. L., Rivera O., Thom. W. J., Chu, P. M., and Sams, R. L. Nitrogen Dioxide Formation during Inhaled NO Therapy. Clinical Chemistry 45:3. 382-387 (1999), which is incorporated by reference in its entirety. Special cross purge valve assemblies are commercially available that allow the small volume between the cylinder shut off valve and the gas regulator shut off to be purged of air before use. Unless this is carried out, the air that is trapped there can back stream into the gas cylinder. This will occur each time the gas regulator is re-installed on the gas cylinder. On connecting a two stage gas regulator to a large gas cylinder containing 4,000 liters of compressed calibration gas of NO, the approximately 20 ml of air volume in the regulator would cause the NO to be reduced by 2 ppm on the full cylinder. If the cylinder was certified at 45 ppm NO it would now be reduced to 43 ppm, a 4.4% error. For $NO_2$, and assuming about 70% relative humidity in the room the $NO_2$ would be reduced by about 0.2 ppm. For a cylinder containing only 10 ppm of $NO_2$, this would lead to an error of 2% on a single connection. These errors scale inversely with the volume of the contents and the concentration of the active component. Degradations of the order of 20% from a single failure to properly purge a medium size calibration cylinder that was half consumed have been observed.

In commercial clinical use, small disposable cylinders, that contain 57 liters, pressurized to 500 psi, are frequently used. The certified accuracy of a new NO and $NO_2$ gas mixture, traceable to NIST, are 45 ppm±4% for NO and 10 ppm±10% for $NO_2$. See, Air Liquide. The small disposable cylinders are designed to be used with a single-stage flow-through gas regulator so that the only OPEN/CLOSE valve is on the cylinder itself, thereby minimizing the back streaming of air into the cylinder.

There are several disadvantages of calibrating the embedded NO and $NO_2$ sensors with accurately known gas calibration standards that are stored in high pressure gas cylinders. First, in clinical use, NO is typically delivered to the patient in oxygen (21% to 99%) and up to 100% humidity at 37° C., whereas the NO calibration gas is delivered in pure nitrogen. The $NO_2$ calibration gas standard is delivered in dry air. It is unwise to calibrate using NO in nitrogen, when clinical practice is to use oxygen enriched air where the $O_2$ content could be 21 to 99%. It is especially problematic since $O_2$ and $H_2O$ are known to react rapidly with the NO and $NO_2$ in the gas phase. Second, as reported by Sokol et al (above) care has to be taken to prevent back-streaming of air into the calibration cylinders which decreases the NO content of the calibration gas, resulting in too high a clinical dose. Third, the calibration cylinders are known to degrade with time. Fourth, the manufacture of stable gas standards of NO and $NO_2$ in the low ppm range is extraordinary difficult, and as a result trustworthy standards are difficult and expensive to obtain. Fifth, the accuracy and repeatability of the NO dose that is being delivered to a patient is dependent upon the accuracy and repeatability of the calibration gas standards.

At the present time, hospitals that provide inhaled NO gas to patients calibrate their NO and $NO_2$ sensors using the classical brute-force analytical laboratory technique of using precision gas standards supplied in high-pressure gas cylinders. This method, which is clumsy and time consuming, requires special training of the therapists in the use of high pressure gas cylinders. NO electrochemical sensors are typically calibrated prior to dosing a patient to ensure that the bias voltage (−270 millivolts) has not degraded.

Because of all of these difficulties, an alternative calibration technique described here that eliminates all of the shortcomings of requiring accurately known gas calibration standards stored in high pressure gas cylinders, use of known calibration gases entirely and entirely eliminates the need for gas calibration tanks. Instead of relying on the accuracy and precision of the gas standard and whether or not it had degraded with time, the alternative technique is independent of the precise NO concentration. Instead, the alternative technique is based on the rate of loss of the NO concentration with time as it reacts with $O_2$ to form $NO_2$. The kinetics of the homogeneous gas-phase reaction of NO with $O_2$ to produce $NO_2$ was first studied by Bodenstein and Wachenhein in 1918, as shown in Equation 1. See, Bodenstein, M, Wachenheim L: Die Geschwindigkeit der Reaktion zwischen Stickoxyd and Sauerstoff. Z. Elektrochem: 24, 183-201, 1918, which is incorporated by reference in its entirety.

$$NO+NO+O_2 \xrightarrow{k} NO_2+NO_2 \qquad \text{Equation 1}$$

Since their early research, 22 additional independent experimental studies have been carried out in 6 countries covering the temperature range of 273° K to 600° K, with NO partial pressures ranging from 20 parts per million (ppm) to 2,000 ppm to 200,000 ppm. See, for example, Tsukahara H, Ishida T, and Mayumi M: Gas-Phase Oxidation of NO: Chemical Kinetics and Rate Constant. NO: 3, 191-198, 1999, which is incorporated by reference in its entirety. The intense interest in the reaction was initially due to the mechanism being (pseudo) third order, with a slightly negative temperature coefficient. It was then studied again in the 1960's and 1970's because of NO's importance as an air pollutant, and then again, more recently, because of importance of NO in mammalian biochemistry. There have also been numerous review articles on the kinetics. See, for example, Tsukahara H et al., referred to above. As a result, the reaction of NO with $O_2$ is one of the most well documented gas phase reactions in all of physical chemistry.

The rate of formation of $NO_2$ has been shown to be first order in $O_2$, second order in NO and third order in pressure, with the rate of formation of $NO_2$ being expressed as:

$$+d(NO_2)/dt = -d(NO)/dt = k(NO)^2(O_2) \quad \text{Equation 2}$$

According to the fundamental kinetic rate Equation 2, the rate of formation of $NO_2$, $d(NO_2)/dt$, is equal to the rate of loss of NO, $-d(NO)/dt$. The increase in the concentration of $NO_2$ and the loss of NO over a given time period can be readily determined from the change in output of the NO and $NO_2$ electrochemical sensors. The two sensors nominally provide the identical slope, when normalized to unity, with the $NO_2$ slope being positive and the NO slope being negative. Furthermore, since the rate constant, k, and the corresponding temperature coefficient are well known, the NO concentration can be determined solely by measuring the rate of change of the $NO_2$ and/or the NO concentration with time, provided that the $O_2$ concentration remains constant over the course of the measurement, which is typically true when measuring low ppm concentrations in air (e.g., 21% $O_2$). Prior knowledge of the precise NO concentration is not required. The normalized slopes are then compared to what is expected from the kinetic rate Equation 2.

The kinetic rate Equation 2 is integrated by assuming that the oxygen is present in excess, 21% (210,000 ppm) and is therefore effectively constant, and converting to the appropriate units, the concentration of $NO_2$ (in ppm) present at time t (in seconds) is given by:

$$(NO_2) = \frac{2.28 \times 10^{-7} t (NO)^2_{init} (\% O_2)}{2.28 \times 10^7 t (\% O_2)(NO)_{init} + 1}$$

The rate constant has been established as $k = 2.4 \times 10^9 \exp(1046/RT)$ cm$^6$ mol$^{-2}$ sec. A simple approximation for NO concentrations in the low ppm range gives (see, Fine D. H: Critical evaluation of Saltzman technique for NOx analysis in the 0-100 ppm range. Environ. Sci. Technol: 6, pp 348-350, 1972, which is incorporated by reference in its entirety):

$$NO_2 = 2.28 \times 10^{-7} t (NO)^2_{init} (\% O_2) \quad \text{Equation 3}$$

Equation 3 can be used to calculate the theoretical $NO_2$ concentration using the known rate constant, if the NO and $O_2$ concentration are known.

Figure 1:
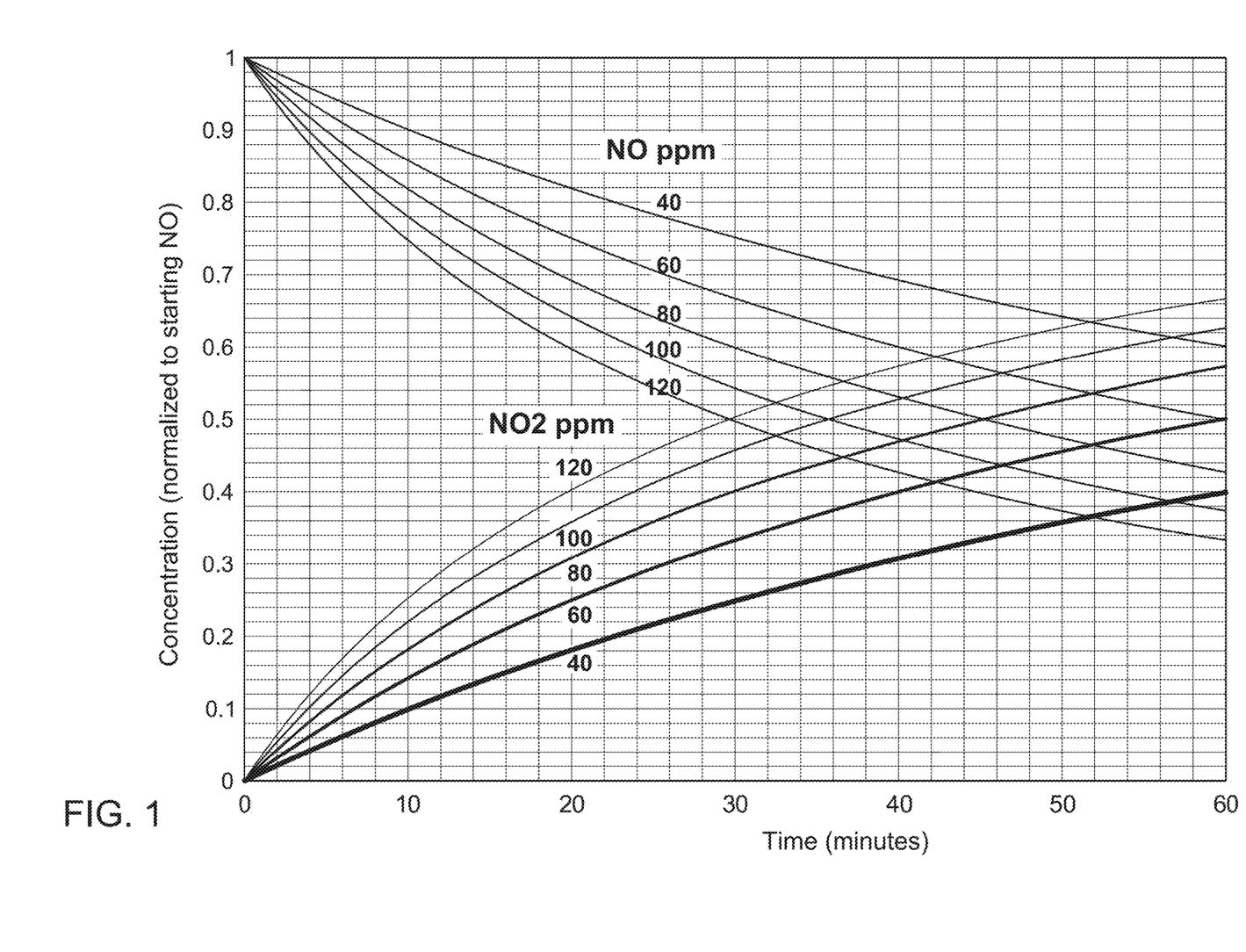
FIG. 1 is a graph of example data depicting the conversion of NO to $NO_2$ as a function of time for up to 60 minutes, NO in ppm. $O_2$=20%, normalized.

Since the signal from the sensors is a function of the gain of the system, all data and ratios are normalized, thus allowing comparison without needing to correct for gain differences. Equation 3 can be used to determine the change of ratio of the NO as a function of time for different NO starting concentrations. As shown in FIG. 1 there is a curvature of the plots over a time period of 60 minutes. FIG. 1 depicts the conversion of NO to $NO_2$ as a function of time for up to 60 minutes, NO in ppm. $O_2$=20%, Normalized.

Figure 2:
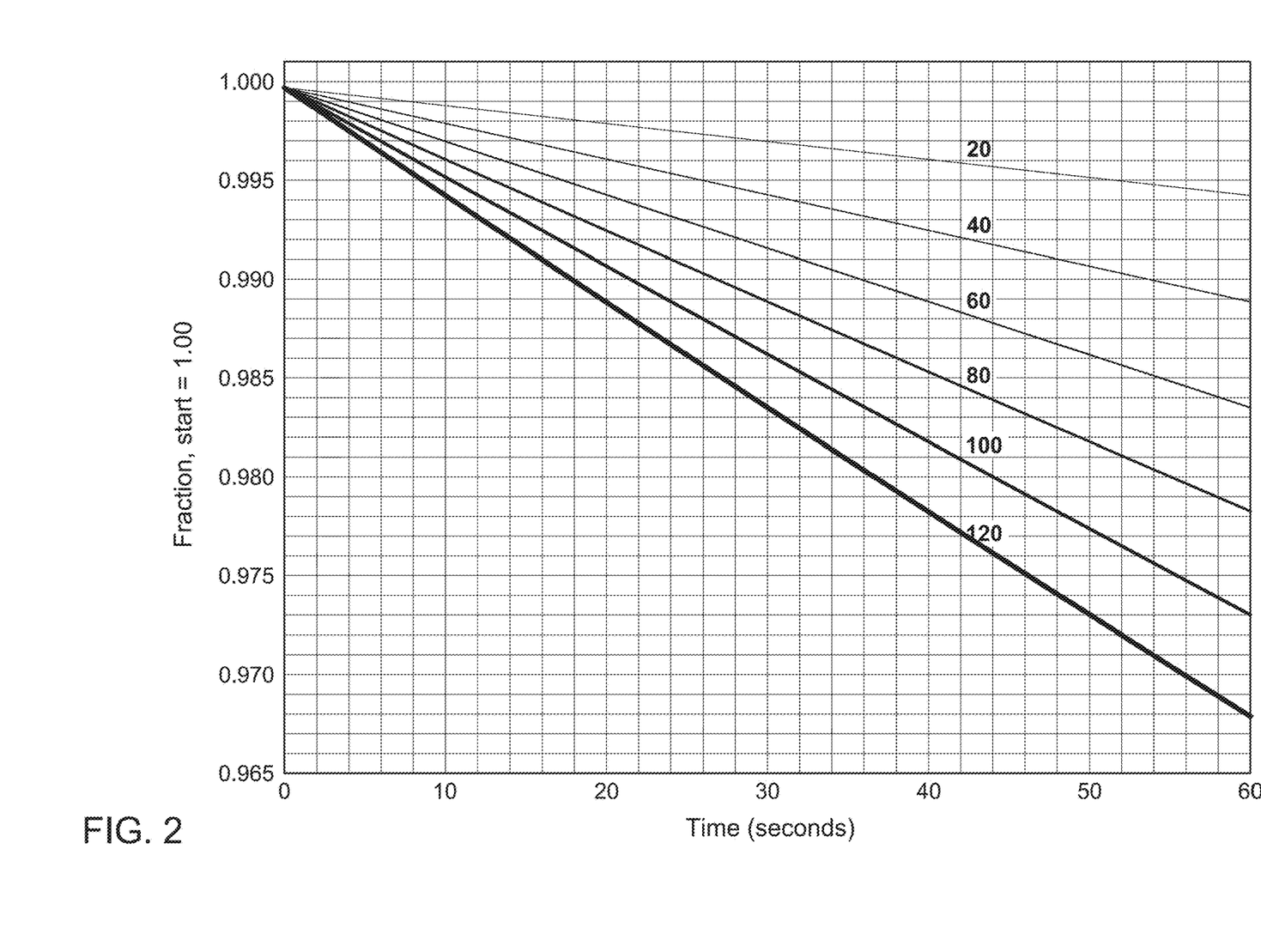
FIG. 2 is a graph of example data depicting the NO fraction as a function of time for up to 1 minute only, NO in ppm, $O_2$=20%, Normalized.

Over a 1-minute time period, which is a convenient time period for a practical calibration, the plots are essentially linear, as shown in FIG. 2. FIG. 2 depicts the NO fraction as a function of time for up to 1 minute only, NO in ppm, $O_2$=20%, Normalized. Note plots are a straight line over the time period of interest.

Figure 3:
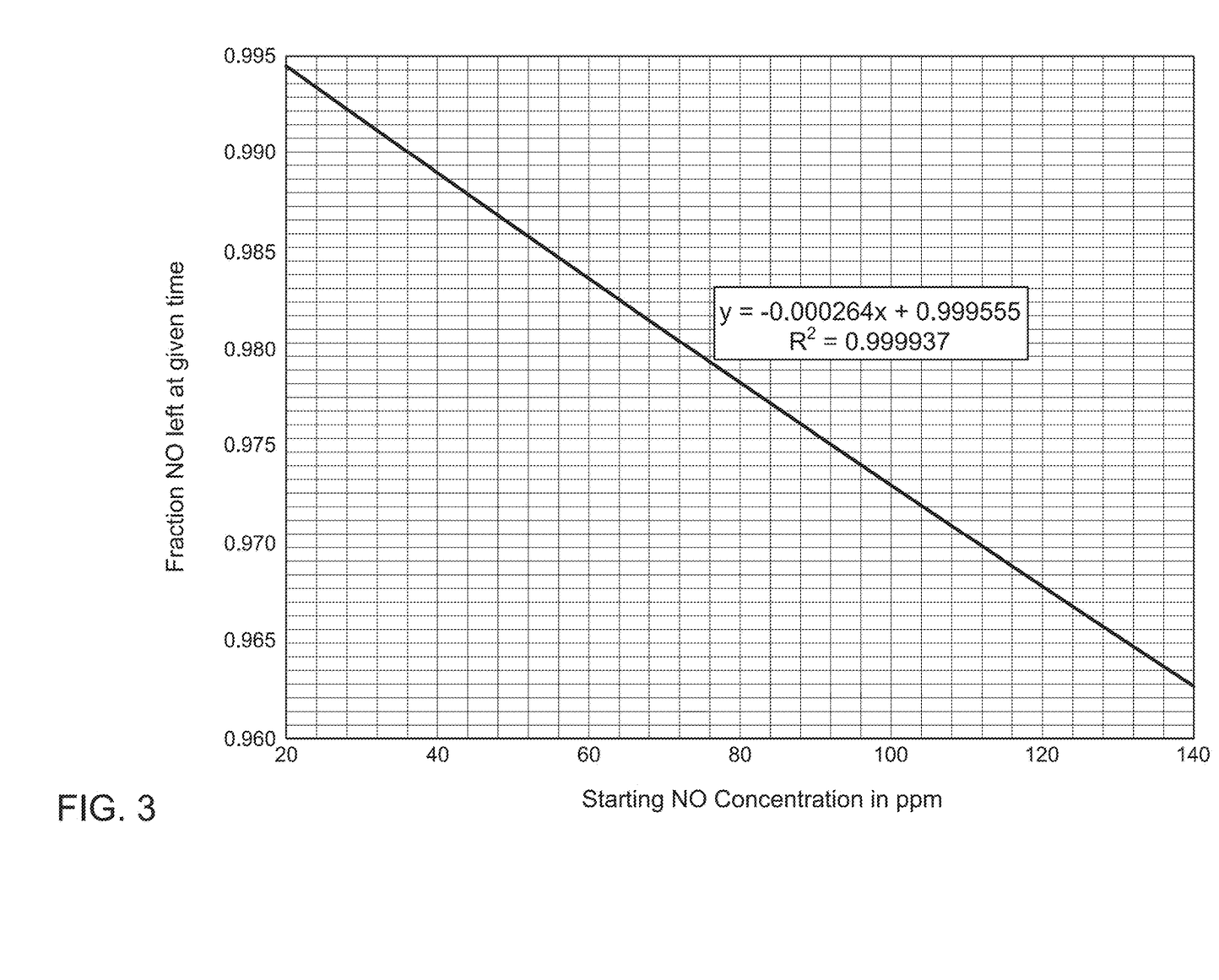
FIG. 3 is a graph of example data depicting the fraction NO remaining at 60 seconds as a function of start time NO Concentration.

From the 60 second vertical data line of FIG. 2, the expected NO ratio at different starting concentrations is shown in FIG. 3. Thus, for any ratio of NO remaining, the starting NO concentration at the beginning of the 60 second time frame can be obtained. The equation of the line is also shown in FIG. 3. FIG. 3 depicts the fraction NO remaining at 60 seconds as a Function of start time NO concentration.

One example of how the method can be used is to fill a small balloon with a gas containing NO in air and measure the rate of loss of NO and the rate of gain of $NO_2$ with time, and then use FIG. 3 to calculate the NO concentration of the gas. In practical terms, this is accomplished by diverting some of the NO in air that is being generated by the system, at a concentration of in the 30 to 100 ppm range, into a 1 liter Tedlar bag, and then withdrawing the gas from the bag as it is emptied into the sampling module of the NO delivery system. Tedlar is the material of choice because it does not tend to hold onto $NO_2$ when used for validating $NO_2$ to NO catalytic converters by the US Environmental Protection Agency (EPA). See, for example, Government Printing Office, Code of Federal Regulations, Determination of Nitrogen Oxides Emissions from stationary sources (instrumental analyzer procedure), Method 7e, Section 16.2, which is incorporated by reference in its entirety. The EPA utilizes Equation 2 as part of the Agency's measurement protocols for enforcement of the Clean Air Act. It is used to check on the efficiency of a $NO_2$ to NO catalytic converter that is used for air monitoring of NO and $NO_2$ using a chemiluminescent analyzer. These converters typically use a molybdenum catalyst operating at 350° C., which is known to degrade with usage and time. If the sum of NO+$NO_2$ concentration drops by more than 2 percent over a 30 minute period, then the $NO_2$ converter has failed to meet the criteria of this EPA test.

Figure 4:
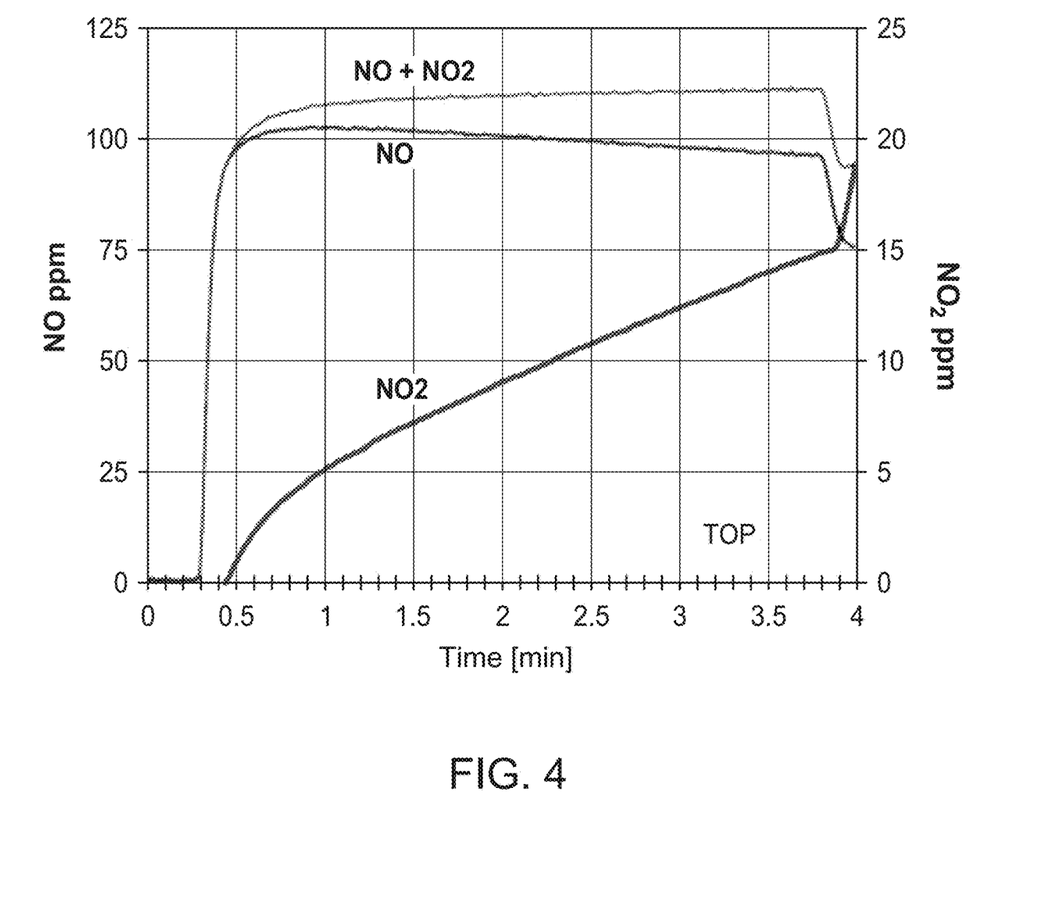
FIG. 4 is a graph that depicts a data plot of the output of the electrochemical sensors, showing the increase in $NO_2$, the decrease in NO and the sum of $NO_2$+NO, according to an embodiment. Note that the vertical axis for the $NO_2$ increase is 5 times greater than the NO decrease.

With a sampling rate of approximately 300 ml/min, a 1 liter bag allows for about 200 seconds of continuous data. FIG. 4 shows an example of the data that is generated, showing the decrease in the NO concentration, the increase in the $NO_2$ concentration with the sum of the NO and $NO_2$ concentrations remaining constant. FIG. 4 depicts a data plot of the output of the electrochemical sensors, showing the increase in $NO_2$, the decrease in NO and the sum of $NO_2$+NO. Note that the vertical axis for the $NO_2$ increase is 5 times greater than the NO decrease. In this example, the same calibration procedure was repeated 21 times over a two day period, with essentially identical results.

While in FIG. 4 it is concentration versus time that is plotted, when the example is integrated into the device it would be the milli-voltage increase above the voltage for zero air that would be measured, but since ratios are used in the analysis, essentially the same result would be obtained without regard to whether voltages or concentrations are used.

From FIG. 4, it can be seen that initially there is a stabilization period that occurs once the data collection is started, probably due to the time it takes for the sample to reach the sensors and for the sensors to respond, and then there is a drop off as the content of the bag is exhausted, which is to be expected since the Tedlar bag is only about 1 liter in size. In certain circumstances, the data used to check calibration can be collected over a 60 second period ending slightly before the drop off.

From FIG. 3 it can be seen that the equation of the starting NO concentration versus ratio or starting fraction for the condition where data is collected over a 60 second period is:

$$Y = -0.000264x + 0.999555.$$

Substituting the experimental ratio computed as described above for Y one may calculate the starting NO concentration x.

A calibration technique for the NO and $NO_2$ electrochemical sensors is shown in the following example:

A gas sample in the 30 to 80 ppm NO range in air is used to fill a 1-liter Tedlar bag. Optionally, a 0.5 liter or 0.75 liter Tedlar bag can be used. The Tedlar bag can be contained inside a small box or tube, so as to protect it from damage. The Tedlar bag can be located inside the device console, or external to it. For the NO platform that generates the source gas, NO in air from the source is diverted to the Tedlar bag. For a system that uses a gas cylinder as the source of typically 800 ppm of NO in nitrogen as the source, air and the NO gas source are mixed in the Tedlar bag. The nature of the NO source gas or its concentration, are not material provided that the NO concentration is within the operating range of the sensor.

The calibration check and/or a complete calibration is performed by activating the calibration button on the touch screen. The sampling module of the NO delivery system is activated and the air from the Tedlar bag containing NO is analyzed by passing it through the sampling module and past the NO, and/or the $NO_2$ and/or the $O_2$ sensors.

The electrochemical sensors of the sampling module are used to measure the change in NO and $NO_2$ response over a time frame of a fraction of a minute to several minutes, or until the Tedlar bag is empty. The sensors have a linear response and the measurement entails an accurate determination of the milli-voltage output of the sensors over time. FIG. 4 shows a typical plot of the voltage output versus time for NO, $NO_2$ and the sum of $NO+NO_2$.

The calibration is deemed to be valid when the data needs to show the following:

The linear regression analysis of the slope of the NO and/or $NO_2$ concentration with time, as shown in FIG. 4, is >0.99. A much lower number would imply that there was too much scatter in the data, or that the sensor was damaged.

The rate of loss of NO is essentially equal (e.g., within 1%, 5% or any other suitable percentage) to the rate of gain of $NO_2$, such that $NO+NO_2$ is a constant. This check assures that both the NO and the $NO_2$ sensors are working properly.

The normalized slope (rate of change of the concentration with time) is used to calculate or look up the NO concentration at the beginning of the slope calculation, or a calculation can be made using the equations derived here.

If the concentration as calculated from the slope is within the expected range from determined by the sensors, then the calibration serves as a span check and no changes are necessary.

If the calculated concentration differs from the output of the sensors by more than the error range, then the calibration of the settings can be modified. If the calibration shows that one or more sensors have drifted, then the system modifies the calibration settings and resets the calibration settings.

If the sum of the NO and $NO_2$ sensor normalized output is not constant, then either the NO or the $NO_2$ sensor is not working properly. If the system has twin NO sensors then it is possible to diagnose which sensor has failed to calibrate properly. If the two NO sensors are in agreement, but the sum of NO and $NO_2$ is not constant, then the $NO_2$ sensor is bad. If the two NO sensors do not agree with each other, then the one that has its value and the $NO_2$ value as a constant is the good one, and the other NO sensor is the bad sensor.

An essentially similar procedure can be used to calibrate air pollution sensors and monitors that measure NO and $NO_2$ and NOx, which is the sum of NO and $NO_2$. The information described herein can also be used to calibrate many other instruments and technologies, where one or more of the components is formed during the process, and where the kinetics of the reaction are known. The method is especially relevant where the rate of change of the component of interest varies non-linearly with time. Measurement of the rate of change of an analyte with time can be used to calibrate the concentration of the analyte of interest, instead of calibrating with one or more accurately known standards. The application is especially important and valuable when measuring low concentrations in the low ppm range or below, where it is difficult or impossible to store accurately known standards, which typically degrade with time. The procedure applies equally well to both gas phase standards and analytes dissolved in ionic or non-ionic fluids. For the technique to be viable, the decomposition rate or the reaction rate of the analyte of interest should be well known, and that the calibration is linear in the concentration range of interest. The accuracy is enhanced if the decomposition rate or the reaction rate of one of either the analyte or the decomposition product varies in a non-linear way with concentration.

Because the zero of an electrochemical sensor is known to drift, especially with temperature, sensors can be particularly sensitive to zero point calibrations. Performing the zero calibration can be simple and quick since it can be performed using room air and can be performed in the short period of time that it takes for the cassette that produces the NO gas to heat up to operational temperature and stabilize. If very high precision is required for the zero calibration for an NO or $NO_2$ sensor, the room air can be scrubbed, for example, with a permanganate scrubber to remove any NO or $NO_2$ that may be present in the room air. High precision close to zero is particularly important for devices during weaning at or below 1 ppm, and for long term dosing of patients at NO levels in the 0.1 to 2 ppm range.

The second data point is challenging the sensor with a known amount, typically greater than 50% of full scale response of the sensor. The high concentration calibration is a more difficult since a source of gas of known concentration is required. The devices can be calibrated as described above.

Alternatively, the following approaches, while less accurate and therefore less desirable, may be employed in some situations.

The gas sensors can be calibrated at the factory, and any time the device is serviced by qualified technicians. The on board computer can keep track of the actual concentration being measured. If the concentration drifts downward by a few percent with each cassette a message to calibrate could be generated before the calibration had shifted significantly. If it was a onetime occurrence, and the next cassette was within calibration, then it could be assumed that the original cassette was off (e.g., defective). The zero calibration data point can be effective to keep the NO and $NO_2$ sensors accurately calibrated, since the dominant drift with time is the zero drift. Zero drift can be assessed each time a new cassette is used.

The long term drift of the full scale output of the electrochemical sensors is typically relatively small, even over many months, as compared to the zero drift which is also highly dependent upon temperature. The sensor can be routinely checked using the method described above.

Figure 5:
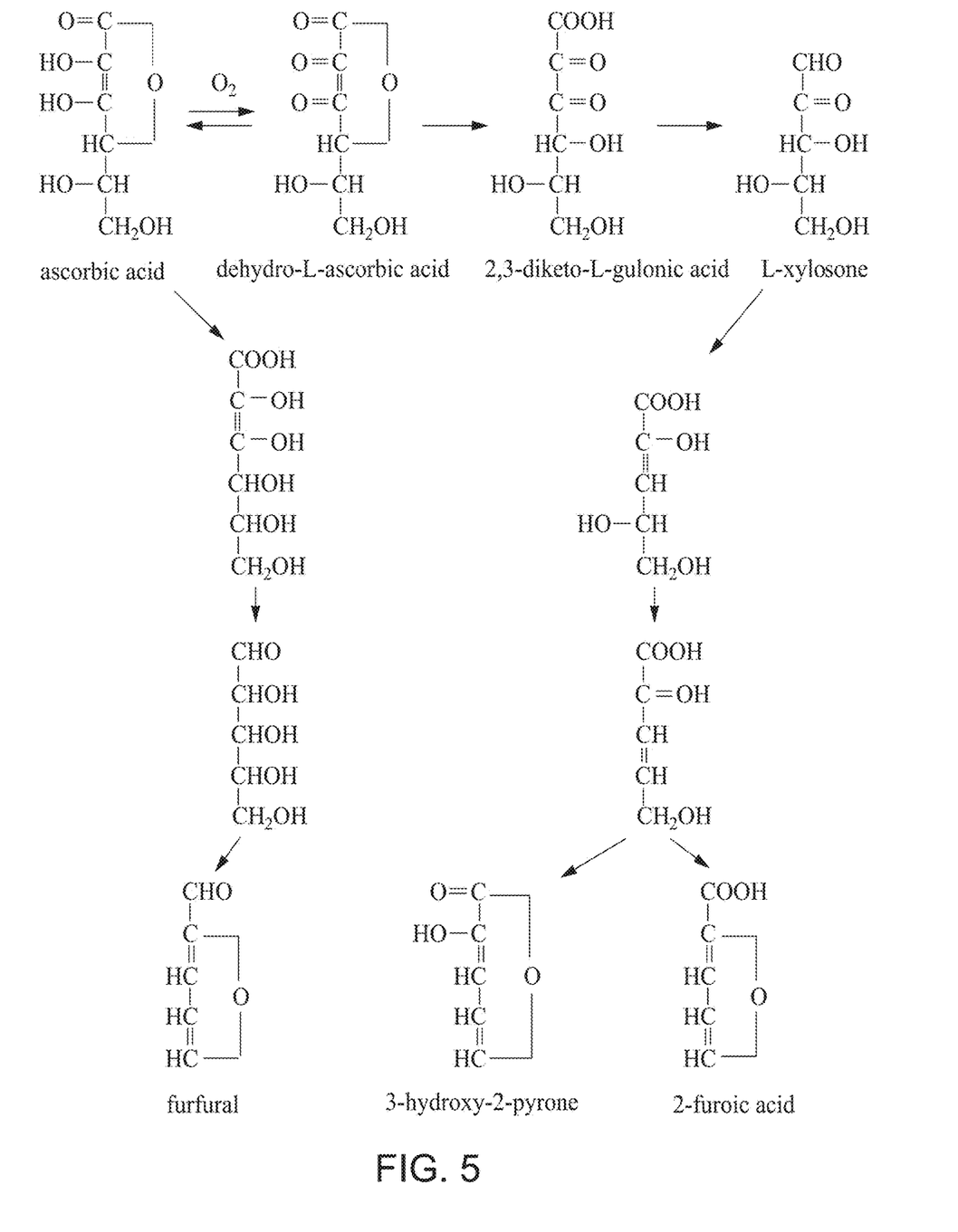
FIG. 5 shows the possible reaction pathways for the degradation of ascorbic acid.

The new calibration technique that is described here for gases, can be applied to any other suitable analyte in ionic and non-ionic liquid solutions, which are far too numerous to list, even by general categories. A specific example is the decomposition of ascorbic acid in aqueous solutions at different pH values. See, for example, Yuan, J-P. and Chen, F., Degradation of Ascorbic Acid in Aqueous Solution, *J. Agric. Food Chem.* 1998, 46, 5078-5082), which is referenced here in its entirety. They found that after ascorbic acid aqueous solutions were heated at 100° C. for 2 hours, three main degradation products, furfural, 2-furoic acid, and 3-hydroxy-2-pyrone, were found. In an acid aqueous solution, ascorbic acid was converted to 2-furoic acid and 3-hydroxy-2-pyrone via dehydroascorbic acid under aerobic conditions, whereas under anaerobic conditions, ascorbic acid degraded to furfural. The chemistry is shown in FIG. 5. Low pH conditions favored the formation of furfural, 2-furoic acid, and 3-hydroxy-2-pyrone; at extremely low pH (i.e., pH 1), the formation of furfural dominated at pH 10, only very small amounts of furfural and 3-hydroxy-2-pyrone with no 2-furoic acid were detected. They concluded that in a hydrogen-ion-catalyzed environment, the anaerobic degradation of ascorbic acid to furfural was the main degradation pathway in an aqueous solution. This data can now be used at a particular pH to determine the rate of loss of ascorbic acid and the rate of formation of furfural, and the information used to set up a calibration based on the amount of furfural formed over time, and used to calculate the ascorbic acid concentration at time zero.

Details of one or more embodiments are set forth in the accompanying drawings and description. Other features, objects, and advantages will be apparent from the description, drawings, and claims. Although a number of embodiments of the invention have been described, it will be understood that various modifications may be made without departing from the spirit and scope of the invention. It should also be understood that the appended drawings are not necessarily to scale, presenting a somewhat simplified representation of various features and basic principles of the invention.

What is claimed:

1. A method, comprising:
   collecting a sample of a gas containing nitric oxide (NO) and oxygen in a container;
   measuring a rate of a decrease in an NO signal over a period of time, the NO signal produced by a first electrochemical sensor based on a concentration of NO in the container;
   determining based on the rate of the decrease in the NO signal, a concentration of NO in the gas at a time before any NO in the gas reacted with oxygen; and
   adjusting a calibration parameter of the first electrochemical sensor based on the concentration of NO in the gas at the time before any NO in the gas reacted with oxygen.

2. The method of claim 1, wherein:
   the gas is a first gas; and
   collecting the sample includes directing a second gas containing NO to the container, the second gas being devoid of oxygen and $NO_2$, the method further comprising:
   mixing the second gas within the container with a third gas to produce the first gas.

3. The method of claim 1, wherein:
   the gas is a first gas; and
   collecting the sample includes directing a second gas containing NO to the container, the second gas being devoid of oxygen and $NO_2$, the method further comprising:
   mixing the second gas within the container with a third gas to produce the first gas at a first time, the first time being the time before any NO in the gas reacted with oxygen.

4. The method of claim 1, wherein:
   the gas is a first gas; and
   collecting the sample includes directing a second gas containing NO to the container, the second gas being devoid of oxygen and $NO_2$, the method further comprising; and
   mixing a volume of the second gas within the container with a volume of a third gas to produce the first gas, the volume of the third gas being between 100 and 10,000 times larger than the volume of the second gas.

5. The method of claim 1, wherein collecting the sample includes:
   diverting a source gas to the container, the source gas containing NO at a concentration between 30 ppm and 80 ppm in air.

6. The method of claim 1, further comprising:
   measuring a rate of an increase in an $NO_2$ signal over the period of time, the $NO_2$ signal produced by a second electrochemical sensor based on a concentration of $NO_2$ in the container; and
   determining based on the rate of the decrease in the NO signal and the rate of the increase in the $NO_2$ signal, the concentration of NO in the gas at the time before any NO in the gas reacted with oxygen.

7. The method of claim 6, further comprising:
   comparing a sum of the NO signal and the $NO_2$ signal; and
   sending an indication of a calibration failure based on the sum of the NO signal and the $NO_2$ signal varying during the period of time.

8. The method of claim 1, wherein the period of time is between 30 seconds and 4 min.

9. A method, comprising
   collecting a sample of a gas containing nitric oxide (NO) and oxygen in a container;
   measuring a rate of a decrease in an NO signal over a period of time, the NO signal produced by a first electrochemical sensor based on a concentration of NO in the container;
   determining based on the rate of the decrease in the NO signal a concentration of NO in the gas; and
   adjusting a calibration parameter of the first electrochemical sensor based on the concentration of NO in the gas.

10. The method of claim 9, wherein:
    the gas is a first gas; and
    collecting the sample includes directing a second gas containing NO to the container, the second gas being devoid of oxygen and $NO_2$, the method further comprising:
    mixing the second gas within the container with a third gas to produce the first gas.

11. The method of claim 10, wherein the concentration of NO in the gas is determined at a time when the second gas is mixed with the third gas and before any NO in the second gas has reacted with oxygen.

12. The method of claim 9, wherein:
    the gas is a first gas; and
    collecting the sample includes directing a second gas containing NO to the container, the second gas being devoid of oxygen and $NO_2$, the method further comprising; and
    mixing a volume of the second gas within the container with a volume of a third gas to produce the first gas, the volume of the third gas being between 100 and 10,000 times larger than the volume of the second gas.

13. The method of claim 9, wherein collecting the sample of NO includes:
diverting a source of gas to the container, the source of gas containing NO at a concentration between about 30 ppm to about 80 ppm.

14. The method of claim 9, further comprising:
measuring a rate of an increase in an $NO_2$ signal over the period of time, the $NO_2$ signal produced by a second electrochemical sensor based on a concentration of $NO_2$ in the container; and
determining based on the rate of the decrease in the NO signal and the rate of the increase in the $NO_2$ signal, the concentration of NO in the gas.

15. The method of claim 14, further comprising:
measuring a rate of an increase in an $NO_2$ signal over the period of time, the $NO_2$ signal produced by a second electrochemical sensor based on a concentration of $NO_2$ in the container;
determining based on the rate of the decrease in the NO signal and the rate of the increase in the $NO_2$ signal, the concentration of NO in the gas at the time before any NO in the gas reacted with oxygen.

16. The method of claim 9, wherein the period of time is between about 30 seconds to about 4 min.

17. The method of claim 9, further comprising:
measuring a rate of an increase in an $NO_2$ signal over the period of time, the $NO_2$ signal produced by a second electrochemical sensor based on a concentration of $NO_2$ in the container;
determining based on the rate of the decrease in the $NO_2$ signal, the concentration of $NO_2$ in the gas; and
adjusting a calibration parameter of the second electrochemical sensor based on the concentration of $NO_2$ in the gas.

18. A method, comprising
collecting a sample of a gas containing nitric oxide (NO) and oxygen in a container;
measuring a rate of an increase in an $NO_2$ signal over a period of time, the $NO_2$ signal produced by an electrochemical sensor based on a concentration of $NO_2$ in the container;
determining based on the rate of the increase in the $NO_2$ signal a concentration of $NO_2$ in the gas; and
adjusting a calibration parameter of the electrochemical sensor based on the concentration of $NO_2$ in the gas.

19. The method of claim 18, wherein the electrochemical sensor is a first electrochemical sensor, the method further comprising:
measuring a rate of a decrease in an NO signal over the period of time, the NO signal produced by a second electrochemical sensor based on a concentration of NO in the container;
determining based on the rate of the increase in the NO signal, the concentration of NO in the gas; and
adjusting a calibration parameter of the second electrochemical sensor based on the concentration of NO in the gas.

* * * * *

UNITED STATES PATENT AND TRADEMARK OFFICE
CERTIFICATE OF CORRECTION

Page 1 of 1

PATENT NO. : 11,243,197 B1
APPLICATION NO. : 16/513274
DATED : February 8, 2022
INVENTOR(S) : Fine et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 257 days.

Signed and Sealed this
Twenty-ninth Day of November, 2022

Katherine Kelly Vidal
*Director of the United States Patent and Trademark Office*